United States Patent [19]

Buhl et al.

[11] Patent Number: 5,413,732
[45] Date of Patent: May 9, 1995

[54] REAGENT COMPOSITIONS FOR ANALYTICAL TESTING

[75] Inventors: Steven N. Buhl, Cupertino; Bhaskar Bhayani, Fremont; Chi-Sou Yu, Saratoga; Thuy N. Tang, San Jose, all of Calif.

[73] Assignee: Abaxis, Inc., Sunnyvale, Calif.

[21] Appl. No.: 747,179

[22] Filed: Aug. 19, 1991

[51] Int. Cl.$^6$ .................... C09K 3/00; G01N 31/00
[52] U.S. Cl. .................... 252/182.11; 436/8; 435/4
[58] Field of Search .............. 435/26, 4; 436/45, 63, 436/805, 808, 8; 264/6, 14, 28, 101; 422/72, 91, 101, 102; 210/781, 782; 252/182.11

[56] References Cited

U.S. PATENT DOCUMENTS

| | | | |
|---|---|---|---|
| 3,721,725 | 3/1973 | Briggs | 264/6 |
| 3,819,488 | 6/1974 | Rush | 195/103.5 R |
| 3,932,943 | 1/1976 | Briggs | 34/5 |
| 4,115,537 | 9/1978 | Driscoll | 424/1 |
| 4,295,280 | 10/1981 | Krupey | 34/5 |
| 4,351,158 | 9/1982 | Hurwitz | 62/60 |
| 4,438,239 | 3/1984 | Rembaum et al. | 525/54.1 |
| 4,588,696 | 5/1986 | Eskelson | 436/130 |
| 4,671,954 | 6/1987 | Goldberg et al. | 424/450 |
| 4,678,812 | 7/1987 | Bollin, Jr. | |
| 4,712,310 | 12/1987 | Roy | 34/5 |
| 4,716,119 | 12/1987 | Rehner | 436/16 |
| 4,755,461 | 7/1988 | Lawson | 435/13 |
| 4,762,857 | 8/1988 | Bollin, Jr. | |
| 4,820,627 | 4/1989 | McGeehan | 435/4 |
| 4,828,982 | 5/1989 | Wagner | 435/7 |
| 4,848,094 | 7/1989 | Davis | 62/64 |
| 4,859,606 | 8/1989 | Cran et al. | 436/79 |
| 5,008,116 | 4/1991 | Cahn | 424/491 |
| 5,122,284 | 6/1992 | Braynin et al. | 210/782 |

FOREIGN PATENT DOCUMENTS 85155 2/1985 Romania .

OTHER PUBLICATIONS

Clin. Chem. 29(9) 1609–1615 (1983).
Driscoll, et al., *Clin. Chem.* 29:1609–1615 (1983).

*Primary Examiner*—Douglas W. Robinson
*Assistant Examiner*—A. Varma
*Attorney, Agent, or Firm*—Townsend and Townsend Khourie and Crew

[57] ABSTRACT

The present invention provides lyophilized reagent spheres comprising reagents suitable for analysis of biological samples, in particular analysis of blood samples in centrifugal analyzers. Also provided are diluents which are conveniently used in such analyzers.

6 Claims, No Drawings

REAGENT COMPOSITIONS FOR ANALYTICAL TESTING

BACKGROUND OF THE INVENTION

1. Field of Invention

This invention relates to novel reagent compositions and to methods for their preparation. In particular, it relates to novel lyophilized reagent spheres and diluents useful in the analysis of biological samples.

In preparing reagents for convenient and efficient testing of clinical biological samples, it is frequently important to obtain dry chemical blends in uniform, discrete amounts. These reagents must be efficiently and economically prepared in small precisely measured quantities. Reagents comprising organic materials, however, tend to spoil or degrade on storage, thus creating quality control problems. Thus, reagents are typically provided in dried form to increase stability. Current technology for producing dry chemical blends involves procedures such as dry blending, spray drying, or fluid bed drying. All three of these procedures, however, have limitations that make them costly, inefficient or difficult to carry out.

In dry blending technology, it is difficult to obtain homogeneous blends of chemicals that have different densities. Moreover, homogeneity is particularly difficult to achieve when very small amounts of ingredients are mixed with large amounts of others. Once made homogeneous, it is extremely difficult to reproducibly (within 1 percent) dispense small amounts (less than about 10 mg) of the blended chemicals.

Spray drying technology provides more homogenous blends of chemicals because the reagents are first dissolved in liquid. Using spray drying, however, it is difficult and costly to obtain precisely sized amounts of blended chemicals. As generally practiced, this process yields particles with size distributions having coefficients of variation greater than 20 percent. The resulting particles have to be reprocessed (usually agglomerated) to obtain uniform particle sizes. After agglomeration, the particles are generally less soluble than the original spray dried particles. Moreover, these procedures typically use fluorocarbon cryogenic solutions which are hazardous to the environment.

Fluid bed technology relies upon spraying a liquid reagent blend onto a particle and drying the liquid to obtain a particle coated with the blended reagents. Using this procedure, it is difficult to obtain uniformly sized particles and to produce a uniform coating.

Of particular interest to the present invention are reagents useful in analyzing biological samples, such as blood plasma or serum, in centrifugal analyzers. The rotors used in such analyzers measure volumes of the sample to be tested, mix the sample with an appropriate diluent and separate fluid from cellular components. The rotors also provide a plurality of separate test wells containing chemical reagents in which discrete volumes are optically tested.

Analysis of biological samples in the test wells of centrifugal rotors impose a number of requirements on the reagents used for analysis. In particular, because the analysis is typically highly automated, speed of analysis is at a premium. In addition, many clinical diagnostic analyses require that measurements be made within a short time after the sample is added to the reagent. Thus, the dried reagent preparations must dissolve quickly in the sample solution. In addition, rapid rehydration of the reagents can cause bubble formation, which adversely affects results by interfering with optical measurement.

In centrifugal analyzers, the sample is typically mixed with a diluent before analysis. It is not possible to directly measure the amount of diluent added while the diluted sample is in the rotor. Obviously, improperly diluted samples will produce erroneous results. Thus, convenient methods for determining amount of dilution of the sample in situ are required. In addition, if the sample to be diluted comprises cells, the diluent must contain isotonic concentrations of compounds to prevent osmotic shock to the cells. Such compounds, however, must not enhance or inhibit any of the analyses. Many isotonic solutions are disclosed in the prior art, including saline, glucose, or phosphate buffered saline solutions. None of these solutions are suitable because they can affect results, because they provide additional buffering capacity to the solution or because they add chemicals which are the same as the analytes of interest.

The prior art thus lacks reagent compositions which avoid the above problems in centrifugal analyzers. In particular, the prior art lacks economical and reliable reagent preparations which dissolve quickly in sample solutions and avoid bubble formation. Moreover, currently available diluents are not suitable because dilution cannot be easily measured and they can alter the results of the analysis. The present application addresses these and related problems.

2. Description of Background Art

U.S. Pat. Nos. 3,721,725 and 3,932,943 relate to methods for producing lyophilized reagents comprising spraying a solution containing the reagents into a moving bath of fluorocarbon refrigerants and lyophilizing the resultant frozen droplets. U.S. Pat. No. 4,848,094 discloses methods for the generation of essentially spherical frozen droplets and improved methods for removing frozen droplets from a cryogenic liquid. U.S. Pat. No. 4,655,047 describes methods for freezing drops of relatively thick liquids by dropping them from a small height into a cryogenic material. U.S. Pat. No. 3,819,488 provides stable lyophilized diagnostic compositions for determining glutamic oxalic transaminase and glutamic pyruvic transaminase activities. U.S. Pat. No. 4,588,696 relates to preparation of tablets used in testing for formaldehyde and/or glutaraldehyde. U.S. Pat. Nos. 4,295,280, 4,351,158, and 4,712,310 all relate to methods for preparing homogenous preparations comprising compounds which are incompatible. U. S. Pat. No. 4,820,627 discloses a fluidized bed process for preparing particles suitable for tableting into diagnostic reagents. U. S. Pat. No. 4,115,537 relates to diagnostic tablets containing ion exchange resins. U.S. Pat. No. 4,755,461 is directed to tableted blood plasma compositions. U.S. Pat. Nos. 4,678,812 and 4,762,857 both relate to diagnostic tablets comprising trehalose as an excipient and stabilizer. The use of TRITON ® X-100 is also disclosed. U.S. Pat. No. 4,716,119 discloses the addition of tetramethylammonium acetate to blood serum. Romanian Patent Appln. No. 85,155 relates to enzymatic alkaline phosphotase reagent tablets comprising p-nitrophenyl phosphate. Driscoll et al., *Clin. Chem.*, 29:1609–1615 (1983) discloses an instrument/reagent system comprising tableted reagents for performing photometric assays.

SUMMARY OF THE INVENTION

The present invention is directed to compositions for analyzing biological samples. In particular, it is directed to reagent spheres comprising reagents for analyzing the sample and methods for producing the reagent spheres. The reagent spheres of the present invention are capable of quickly and completely dissolving in a solution, typically in less than about ten seconds. The reagent spheres have a diameter between about 1.7 mm and about 2.3 mm and have a coefficient of weight variation less than about 3%. The reagent spheres comprise, in addition to the reagents necessary for analysis of the biological sample, a surfactant at a concentration sufficient to inhibit bubble formation when the sphere dissolves and a filler in a concentration sufficient to facilitate formation of a chemical lattice capable of conducting water into the reagent sphere.

The surfactant is typically a non-ionic detergent such as octoxynol 9 (TRITON ® X-100) or polyoxyethylene 9 lauryl ether. Concentration of the surfactant in the reagent sphere is typically adjusted such that the concentration in the reconstituted reagent is between about 0.08g and about 3.1g per 100 ml.

Fillers suitable for use in the present invention are polyethyleneglycol, myo-inositol, polyvinylpyrrolidone, bovine serum albumin, dextran, mannitol, sodium cholate or a combination thereof. The filler compounds are typically present in concentration between about 10% and about 50% by dry weight. The chemical lattice formed by the filler compounds allows the reagent sphere to quickly and completely dissolve in a sample solution or diluent.

Reagent spheres are formed by preparing (an aqueous solution) of the appropriate reagent(s), dispensing uniform, precisely measured drops of the aqueous solution into a cryogenic liquid, and lyophilizing the frozen drops. The cryogenic liquid is typically liquid nitrogen which is not agitated.

Also provided are diluents suitable for mixing with a biological sample before optically analyzing the sample. Diluents of the present invention comprise an isotonic concentration of a compound which does not interfere with the analysis of the sample. In particular, the preferred compound will have substantially no buffer capacity at the pH of the particular assay. Typical compounds for this use include tetramethylammonium acetate at a concentration between about 120 mM and about 150 mM and inositol between about 20 and about 30 g/L. The diluent may also comprise a photometrically-detectable marker compound for determining the dilution of the biological sample. Typical marker compounds include dyes such as 1,1', 3,3,3', 3'-hexamethylindotricarbocyanine iodide, 1,1'-bis(sulfoalkyl)-3,3, 3', 3'-tetramethylindotricarbocyanine salts, enzyme substrates (such as lactate and p-nitrophenylphosphate) and enzymes (such as D-lactate dehydrogenase and microbial glucose-6-phosphate dehydrogenase).

DETAILED DESCRIPTION OF THE PREFERRED EMBODIMENTS

The present invention provides compositions for analyzing biological samples in, for example, centrifugal rotors and analyzers which allow rapid and economical analysis of blood samples. Lyophilized reagent spheres are provided that comprise a chemical lattice to facilitate rapid and complete dissolution of the spheres in an aqueous solution. They also comprise a surfactant at a concentration sufficient to inhibit bubble formation as the reagent spheres dissolve. The reagent spheres may be used in combination with diluent solutions comprising isotonic concentrations of compounds having substantially no effect on the assays. In addition, marker compounds are used to quickly and easily determine dilution of the sample in situ.

The reagent spheres and diluents of the present invention are suitable for use in centrifugal analyzers for optically analyzing biologicalfluids, in particular blood plasma or serum. Centrifugal rotors used in such analyzers typically comprise means for mixing the blood with an appropriate diluent and separating plasma from cellular material. The rotors also provide for distribution of the diluted plasma into a plurality of cuvettes within the rotor so that different optical analytic procedures may be performed without having to transfer aliquots of the fluid from the apparatus. One or more reagent spheres comprising the reagents necessary for a desired assay are provided in each cuvette.

The rotors and methods described in the following copending applications are preferably used: U.S. Ser. No. 532,524, filed Jun. 24, 1990, now U.S. Pat. No. 5,061,381 and three applications filed Apr. 1, 1990 (U.S. Ser. Nos. 678,823, 678,824, and 07/678,762 U.S. Pat. Nos. 5,173,193; 5,122,284 and 5,186,844 respectively.). The entire disclosure of these applications are incorporated herein by reference. The above applications disclose centrifugal rotors for separating plasma from whole blood that include a plurality of internal chambers and passages for combining blood plasma or serum with one or more reagents and distributing the plasma or serum to a plurality of individual test wells. The chambers and passages necessary for separating the whole blood into plasma are located radially outward from metering chambers that deliver precisely measured volumes of blood and/or diluent to a separation chamber. The separation chamber includes a radially-outward cell trap. Spinning of the rotor causes the cellular components of the whole blood to be sequestered in the cell trap. The separated plasma is then delivered to a plurality of test wells or cuvettes. The above separation and aliquoting steps typically occur as a result of centrifugal force generated by the spinning rotor.

The compositions of the present invention in combination with the rotors described above are particularly suitable for analyzing blood plasma or diluted blood plasma. They are also useful with a wide variety of other biological fluids, such as urine, sputum, semen, saliva, ocular lens fluid, cerebral fluid, spinal fluid, amniotic fluid, and tissue culture media, as well as food and industrial chemicals, and the like.

The compositions of the present invention are particularly suitable for performing a wide variety of analytic procedures which are beneficially or necessarily performed on blood plasma or diluted plasma. The analytic procedures will generally require that the blood plasma be combined with one or more reagents so that some optically detectable change occurs in the plasma which may be related to measurement of a particular component or characteristic of the plasma. Preferably, the plasma will undergo a reaction or other change which results in a change in color, fluorescence, luminescence, or the like, which may be measured by conventional spectrophotometers, fluorometers, light detectors, etc. In some cases, immunoassays and other specific binding assays may be performed in the test wells. Generally, however, such assay procedures must be homogeneous and do not require a separation step. In other cases, it will be possible to accommodate heterogeneous assay systems by providing a means to separate blood plasma from the test wells after an immunological reaction step has occurred.

Conventional blood assays which may be performed include glucose, lactate dehydrogenase, serum glutamic-oxaloacetic transaminase (SGOT), serum glutamic-pyruvic transaminase (SGPT), blood urea (nitrogen) (BUN), total protein, alkalinity, alkaline phosphatase, c-reactive protein bilirubin, calcium, chloride, sodium, potassium, magnesium, and the like. This list is not exhaustive and is intended merely as being exemplary of the assays which may be performed using the apparatus and method of the present invention. Usually, these tests will require that the blood plasma be combined with one or more reagents which result in a visually detectable, usually photometrically detectable, change in the plasma.

Thus, the reagent spheres of the present invention are prepared from reagents suitable for any of the above analytical assays. Typically, an aqueous solution comprising the reagents is prepared. To ensure uniform composition of the reagent spheres, the solution must be homogeneous and all constituents must be fully dissolved or in suspension. Individual drops of the solution are then dispensed into a cryogenic liquid, preferably liquid nitrogen. A cryogenic liquid as used herein refers to a liquified gas having a normal boiling point below about $-75°$ C., preferably below about $-150°$ C.

The frozen masses are then lyophilized to produce the reagent spheres. The reagent spheres typically comprise less than about 6% residual moisture, preferably less than about 3%. Lyophilization is carried out according to standard procedures known in the art. Typically, the frozen drops are lyophilized for about 4 hours to about 24 hours at about 50 to about 450 mTorr, preferably, about 6 hours at about 200 mTorr.

The drops are uniform and precisely measured so that the resulting dried reagent spheres have uniform mass. When the drops are uniform and precisely measured, the imprecision of the mass (coefficient of weight variation) of the reagent spheres prepared from the drops is less than about 3%, and preferably between about 0.3% and about 2.5%. To further decrease the coefficient of weight variation, the aqueous solution is preferably degassed using a vacuum pump or vacuum line before the drops of solution are dispensed.

To obtain values for coefficient of weight variation, known quantities of reagent spheres are weighed. The coefficient of variation (C.V.) is then determined as follows:

$$C.V. = J/\bar{x} \times 100$$

wherein

J = standard deviation (for n sphere) =

$$\left[ \frac{(x - \bar{x})^2}{n - 1} \right]^{\frac{1}{2}}$$

weight of one sphere
mean (for "n" sphere) = $\Sigma x/n$

The uniformity of the reagent spheres produced by this method obviates the need for an additional tableting step to obtain uniform size. The drops can be dispensed by any of a number of means which provide the necessary precision. Typically, an IVEK model AAA pump (N. Springfield, Vt.) is used. The solution is usually dispensed in discrete drops having a volume between about 2.5 $\mu$l and about 4.0 $\mu$l. The exact volume of the drops will depend upon the particular application. For instance, in preparing reagent spheres for total protein determinations, 2.96 $\mu$l drops are typically used, for C-reactive protein and alkaline phosphatase determinations, 2.67 $\mu$l are used. Volumes appropriate for other tests are as follows: SGOT, 4.0 $\mu$l; potassium, 4.0 $\mu$l; creatinine, 4.0 $\mu$l; bilirubin, 2.667 $\mu$l; amylase, 2.667 $\mu$l; cholesterol, 2.667 $\mu$l; uric acid, 3.478 $\mu$l; and glucose, 2,065 $\mu$l.

The reagent spheres of the present invention dissolve quickly in an aqueous sample solution, or diluent. A sample solution of the present invention may be a diluted or undiluted biological sample. The reagent spheres typically dissolve in less than about 30 seconds, preferably less than about 10 seconds. The rapidity of dissolution gives the impression that the reagent sphere "explodes" and distributes the dissolving chemicals throughout the reconstituting volume. Rapid dissolution of the spheres is facilitated by a chemical lattice structure which quickly conducts water into the reagent sphere. To form the chemical lattice, fillers are included in the aqueous solution used to produce the spheres. As the reagent spheres are lyophilized, these molecules facilitate formation of a network of open spaces or a chemical lattice in the spheres. The filler components of the reagent spheres are typically polymeric compounds, such as bovine serum albumin, polyethylene glycol, dextran, Ficoll ® (polysucrose) (Pharmacia LKB Biotechnology, Inc., Piscataway, N.J.), or polyvinylpyrrolidone. In addition, emulsifiers such as sodium cholate and the like are useful as fillers. Monosaccharides and their derivatives, such as mannitol or the polyalcohol, myo-inositol, can also be used. Depending upon the assay, the fillers can be used individually or in combination with one or more of the other filler components.

In addition to fillers, the reagent spheres of the present invention also comprise one or more surfactants at concentrations sufficient to inhibit bubble formation when the spheres are rapidly rehydrated. As described above, bubbles are detrimental to the assays because they interfere with optical measurements. If the reagent spheres comprise surfactants at the appropriate concentrations, however, such problems are avoided. Suitable surfactants include non-ionic detergents such as polyoxyethylene 9 lauryl ether, octoxynol 9, SYNTHRAPOL ® (polyoxethylene akyl alcohol), NP-90, TRYCOL ® 5941, TRYCOL ® (polyoxethylene tridecyl alcohol 6735 and the like. Ionic detergents such as GAFAC ® 560, (polyoxethylene nonylphenyl ether phosphate sodium salt) sodium dodecyl sulfate and the like are also suitable. Typically, the surfactants are present in the reconstituted reagent spheres at a concentration between about 0.08 g and about 3.1 g per 100 ml. The surfactant concentration used will depend upon the particular reagents used in the assay.

The fillers and surfactants used in a particular reagent sphere preparation are preferably selected so as to minimize interference with the assay. Optimization of the these components is facilitated by Table 1 which provides information regarding desired characteristics of fillers and surfactants suitable for use with reagents used in a variety of assays. In addition, the Example section below provides the precise concentrations of filler and surfactant components which have been found to be particularly useful in the exemplified assays.

In order to provide reagent spheres of the correct size in a test well, the components are typically concentrated in the reagent sphere. Upon rehydration with a predetermined volume of sample, the reagents and other components are present in the correct concentration. For instance, the components of the reagent spheres for alkaline phosphate determinations are typically at about 6×concentration and total protein reagents are at about 2.7×concentration. The ideal concentration for the reagents for particular assay can be easily determined, depending upon size of the test well, sample volume, and the like.

polyalcohol which has no buffering capacity, at concentrations from about 2% to about 3%.

The diluents of the present invention may also comprise marker compounds which allow the user to quickly and easily determine dilution in situ. The marker compounds of the present invention are typically photometrically detectable compounds which are added in predetermined or measurable amounts to the diluent. After mixing the diluent with the sample, the concentration of the marker is photometrically determined. This can be done by, for instance, comparing the absorbance of the diluted sample at the appropriate wavelength to standard solutions of known concentration. The ratio of the concentrations of the marker be-

TABLE 1

(g/100 ml)

| | fillers | | | | | | | surfactants | | | | | |
|---|---|---|---|---|---|---|---|---|---|---|---|---|---|
| | PEG 3400 | PEG 8000 | PEG 20M | Dextran | bovine albumin | PVP | inositol | mannitol | Mega 8 | n-Octyl glucoside | Triton X-100 | Trycol | Thesit | cholic acid |
| ALP A | | | 5.40 | | | 0.10 | 1.0 | | | | 0.08 | | | |
| ALP B | | | 5.40 | | | 0.10 | 1.0 | | | | 0.08 | | | |
| Amylase | | 4.00 | | | | | 2.0 | | | | 0.30 | | | |
| AST | | 2.50 | | 2.50 | 2.50 | | | | | | 0.40 | | | |
| BUN | | 4.00 | | | | | | | | | 0.30 | | | |
| Cholesterol (BMD) | | 0.87 | | | 3.70 | | | | | | | | | |
| CRP | | 8.40 | | | | | | | | | 0.30 | | | |
| Greatinine Test | | | | | | | | | | | 0.21 | | | 2.0 |
| Creatintine Blank | | | | | | | | | | | 0.25 | | | 2.0 |
| Glucose | | 1.80 | | | 2.10 | | | | | | 0.30 | | | |
| Plasma Dilution | 6.0 | 1.00 | | | 2.00 | | 1.0 | | | | 0.38 | 2.10 | | 10.0 |
| Rotor O.C.A | 8.0 | | 3.00 | | | | | | | | 0.50 | | | |
| Rotor Q.C.B | 5.0 | | 2.00 | | | | 1.0 | | | | 0.50 | | | |
| Sample Blanking | | 9.60 | | 1.00 | | 0.10 | | 10.00 | 0.20 | 0.20 | 0.80 | | | |
| Temperature Bilirubin Enzyme | | | | 2.00 | | | 1.0 | 6.00 | | | | | | |
| Bilirubin Buffer | | 8.00 | | | | | | | | | | | | |
| Total Protein | 5.00 | 4.00 | 0.50 | | | | | | | | | | 0.143 | 0.5 |
| Triglycerides Blank | | 1.80 | | 3.60 | 3.60 | | | | | | 0.15 | 0.30 | | 0.1 |
| Triglycerides Test | | 1.80 | | 3.60 | 3.60 | | | | | | 0.15 | 0.30 | | 0.1 |
| Uric Acid | | 4.00 | | | | | | | | | 0.24 | | | |

As discussed above, diluents are typically used in assays of biological samples. Diluents for use with samples which contain intact cells, such as whole blood, must comprise isotonic concentrations of compounds to protect the cells from osmotic shock. The presence of the isotonic compounds in the diluent, however, must have substantially no effect on the results of the assay. An isotonic compound has substantially no effect on an assay if its presence leads to less than about a 5% change in the results of a quantitative assay, preferably less than about 2.5%, and most preferably less than about 1%. In particular, additional buffer capacity provided by the isotonic compounds should be minimized. The present invention provides improved diluents comprising isotonic concentrations of compounds which do not interfere with the assays. This is accomplished by, for instance, selecting salts of weak acids with pKa's outside the pH range of the particular assay. A preferred salt of a weak acid for this purpose is tetramethylammonium acetate at a concentration of about 120 to about 150 mM. Other suitable compounds include myo-inositol, a fore and after mixing can then be used to determine the amount of dilution of the sample.

Various photometrically detectable marker compounds can be used. Compounds which can be used in a photometrically detectable color reaction can also be used. Ideally, the marker compound does not absorb at any of the wavelengths used in any of the analyses or cause interference with any subsequent assays performed on the sample. Dyes such as 1,1',3,3,3',3'-hexamethylindotricarbocyanine iodide or 1,1'-bis(sulfoalkyl)-3,3,3',3'-tetramethylindotricarbocyanine salts are typically used. Suitable marker compounds which are converted to photometrically detectable compounds include enzyme substrates not normally present in the sample, such as p-nitrophenyl phosphate or D-lactate. The compound p-nitrophenylphosphate is a substrate for alkaline phosphatase and yields a colored p-nitrophenol reaction product. D-lactate is a substrate for D-lactate dehydrogenase and when used with NAD produces the colored NADH reaction product. Other possible markers suitable for use in the diluent include enzymes themselves if used with substrates either present in the plasma or in the reaction chambers that produce color. The enzymes should not normally be present in the sample. For samples of human origin, typical enzymes include microbial glucose-6-phosphate dehydrogenase and D-lactate dehydrogenase. Obviously, the marker compound is preferably selected so as to minimize interference with any subsequent assays performed on the sample. In cases where the marker compound is unstable and long term storage of the diluent is not practical, the marker or its precursor can be held in the dry state and solubilized near or at the time of its use. Such an example is 1,1'-bis(sulfoalkyl)-3,3,3',3'-tetramethylindotricarbocyanine salts which after solubilization in aqueous solutions aggregates. To prevent these problems, the indocyanine dyes and other unstable dyes are typically stored in a dry form, applied to a solid surface. The solid surface may be, for instance, the wall of a passage, capillary or chamber in the analytical rotor or an inert carrier, such as a polystyrene ball. The surface comprising the adsorbed dye may be placed in any passage or chamber in the analytical rotor, for instance in a passage between the diluent chamber and the mixing chamber, or in the mixing chamber. A suitable isotonic diluent solution then dissolves the dye off the surface at the time of its use. The aqueous diluent is selected according to the particular dye used. For indocyanine dyes, 2.5% myo-inositol is suitable.

The following examples show preparation of reagent spheres for particular assays. These examples are provided by way of illustration and not by way of limitation.

Example 1

Preparation of Reagent Spheres for Total Protein Determination

The following solution was prepared by accurately weighing and dissolving the following chemicals in a container of about 800 ml of deionized or distilled water:
sodium potassium tartrate 37.80 g
sodium hydroxide pellets 28.20 g
cupric sulfate 12.00 g
potassium iodide 12.90 g
sodium carbonate 3.85 g
sodium cholate 5.00 g
polyoxyethylene 9 lauryl ether 1.43 g
polyethylene glycol (FW 3400) 50.00 g
polyethylene glycol (FW 8000) 40.00 g
polyethylene glycol (FW 20,000) 5.00 g It is best to completely dissolve each chemical before adding the next chemical. After the last chemical dissolved, the solution volume was adjusted to 1.0 liter with deionized or distilled water. The solution was filtered through a stack of media that terminated in 0.45 micron porosity. The solution was then degassed using a vacuum pump. The above solution when diluted 37 ml plus 63 ml with water is used to assay Total protein concentration in various clinical samples such as serum or plasma. The sodium carbonate is added as a stabilizer, and polyoxyethylene 9 lauryl ether is added for controlling bubbles during dissolution. Sodium cholate and the various polyethylene glycols are added as fillers to facilitate formation of a chemical lattice during subsequent freeze drying.

The solution was dispensed by an IVEK model AAA pump in discrete 2.96 microliter drops at a rate of 1 to 2 drops-per-second. The discrete amounts of fluid drop through air, form spheres and land on the surface of liquid nitrogen. The surface of the nitrogen does not need to be agitated. After freezing the spheres were dried in Virtis freeze dryer (model no. 12EL console) (Gardener, N.Y.) until their residual moistures were less than 11% of the total remaining mass. A freeze dried reagent sphere prepared according to the above method can be reconstituted with 8 microliters of a mixture of water or diluent (14 parts) and human serum (1 part). The resulting change in absorbance at 550 nm minus the absorbance of a reagent sphere reconstituted with 8 microliters of water or diluent and minus the absorbance of the human serum sample diluted in the same ratio with water plus polyethylene lauryl ether and sodium cholate is proportional to the amount of total protein in the sample.

The imprecision (coefficient of variation) among the 1.78 millimeter diameter spheres is:
dispensed frozen spheres 1.5% at 3.7 mg
freeze dried spheres 2.5% at 0.6 mg Each reagent sphere dissolves in 8 microliters of water or diluent within 5 seconds in a centrifugal analyzer.

Example 2

Preparation of Reagent Spheres for C-Reactive Protein Determination

The following solution was prepared by accurately measuring weighing and dissolving the following chemicals in a container of about 200 mls of deionized or distilled water:
C-reactive protein antibody 0.56 liters
Sodium chloride 25.50 g
HEPES 71.50 g
Triton ® X-100 3.00 g
polyethylene glycol (FW 20,000) 84.00 g It is best to completely dissolve each chemical before adding the next chemical. After the last chemical dissolved, the pH was adjusted to 7.4 with dilute sodium hydroxide and the solution volume was adjusted to 1.0 liter with deionized or distilled water. The solution was filtered through a stack of media that terminated in 0.2 micron porosity. The solution was then degassed.

The above solution when diluted 33 ml plus 67 ml with water or diluent is used to assay C-reactive protein in various clinical samples such as serum or plasma. The sodium chloride is added as a stabilizer and Triton ® X-100 is added for controlling bubbles during dissolution. Polyethylene glycol is added to facilitate the development of turbidity in the analytic reaction and as filler to facilitate formation of a chemical lattice during subsequent freeze drying.

The solution was dispensed by an IVEK model AAA pump in discrete 2.67 microliter drops at a rate of 1 to 2 drops-per-second. The discrete amounts of fluid drop through air, form spheres and land on the surface of liquid nitrogen. The surface of the nitrogen does not need to be agitated. After freezing, the spheres were dried in a Virtis freeze dryer (model no. 12EL console) until their residual moistures were less than 6% of the total remaining mass.

A freeze dried reagent sphere prepared according to the above method can be reconstituted with 8 microliters of a mixture of water or diluent (14 parts) and human serum (1 part). The resulting change in absorbance at 340 nm minus the absorbance of a reagent sphere reconstituted with 8 microliters of water or diluent and minus the absorbance of the human serum sample diluted in the same ratio with water plus Triton ® X 100 is proportional to the amount of C-reactive protein in the sample.

The imprecision (coefficient of variation) among the 1.72 millimeter diameter spheres is:
dispensed frozen spheres 1.7% at 2.9 mg
freeze dried spheres 1.8% at 0.5 mg Each reagent sphere dissolves in 8 microliters of water or diluent within 3 seconds in a centrifugal analyzer.

Example 3

Preparation of Reagent Spheres for Alkaline Phosphatase (ALP) Determination

The following solutions were prepared. ALP part A: The following chemicals were accurately measured, weighed, and dissolved in a container of about 800 mls of deionized or distilled water:
Tris(hydroxymethyl)aminomethane-HCL 10.2 g
HEDTA 2.1 g
magnesium chloride hexahydrate 2.6 g
zinc sulfate heptahydrate 1.7 g
4-nitrophenylphosphate 35.6 g
polyethylene glycol (FW 20,000) 54.0 g
myo-inositol 10.0 g
Triton ® X-100 0.8 Sg
glycerol 6.0 g
polyvinylpyrrolidone (FW 30,000) 1.0 g It is best to completely dissolve each chemical before adding the next chemical. After the last chemical dissolved, the pH was adjusted to 6.8 with dilute 2-amino-2-methyl-1-propanol and the solution volume was adjusted to 1.0 liter with deionized or distilled water. The solution was filtered through a stack of media that terminated in 0.2 micron porosity. The solution was then degassed.

ALP part B: The following chemicals were accurately measured, weighed, and dissolved in a container of about 800 mls of deionized or distilled water:
Tris(hydroxymethyl)aminomethane-HCL 10.2 g
Tris(hydroxymethyl)aminomethane 166.0 g
HEDTA 2.1g
polyethylene glycol (FW 20,000) 54.0 g
myo-inositol 10.0 g
Triton ® X-100 0.8 Sg
2-amino-2-methyl-1-propanol 53.4 g
polyvinylpyrrolidone (FW 30,000) 1.0 g It is best to completely dissolve each chemical before adding the next chemical. After the last chemical dissolved, the pH was adjusted to 10.3 with dilute 2-amino-2-methyl-1-propanol and the solution volume was brought liter with deionized or distilled water. The solution was filtered through a stack of media that terminated in 0.2 micron porosity. The solution was then degassed.

The above solutions when combined in equal volumes of 16.7 ml each and 67 ml of water or diluent are used to assay alkaline phosphatase in various clinical samples such as serum or plasma. The glycerol is added as a stabilizer, Triton ® X-100 is added for controlling bubbles during dissolution. Polyethylene glycol, myo-inositol, and polyvinylpyrrolidone are added as fillers to facilitate formation of a chemical lattice during subsequent freeze drying.

The solutions were dispensed separately by an IVEK model AAA pump in discrete 2.67 microliter drops at a rate of 1 to 2 drops-per-second. The discrete amounts of fluid drop through air, form spheres and land on the surface of liquid nitrogen. The surface of the nitrogen does not need to be agitated. After freezing the spheres were dried in a Virtis freeze dryer (model no. 12EL console) until their residual moistures were less than 6% of the total remaining mass.

One of each, ALP A and ALP B, freeze dried reagent spheres can be reconstituted with 16 microliters of a mixture of water or diluent (14 parts) and human serum (1 part). The resulting rate of change in absorbance at 405 nm is proportional to the amount of alkaline phosphatase in the sample.

The imprecision (coefficient of variation) among the 1.72 millimeter diameter spheres is:

|  | ALP A | ALP B |
| --- | --- | --- |
| dispensed frozen spheres | 0.4% at 2.8 mg | 0.7% at 2.9 mg |
| freeze dried spheres | 1.5% at 0.5 mg | 2.2% at 0.7 mg |

The two reagent spheres dissolve in 16 microliters of water or diluent within 10 seconds in a centrifugal analyzer. The active constituents in this assay are separated to improve reagent stability. One of each of the spheres is placed in the same chamber for the ALP assay.

Example 4

Preparation of Freeze-Dried Concentrated Potassium Reagent Containing Macrocyclic Ionophore Trinitroanilino Cryptahemispherand [2.2] for Potassium Determination The active trinitroanilino cryptahemispherand [2.2] and surfactants (BRIJ ® surfactants) polyoxyethylene 20 cetyl ether were isolated from CHROMOLYTE ™ Potassium Reagent (Technicon Instruments Corp., Tarrytown, N.Y. 10961) using Wide-Pore Butyl, 40µM chromatographic medium (J.T. Baker Inc., Phillipsburg, N.Y. 08865) as follows:

25 g of Wide-Pore Butyl, 40µM chromatographic medium were suspended in 360 ml of degassed isopropanol and then 360 ml of degassed deionized water was added. About 80% of the liquid was decanted. An additional 360 ml portion of degassed deionized water was added and the slurry in the flask was sonicated for two minutes, followed by two minutes of vacuum degassing. The suspended chromatographic medium was poured into an appropriately sized chromatographic column to form a 3–10 cm high packing bed. The packing was equilibrated by passing 250 ml of degassed deionized water through the column.

Five liters of ChromoLyte ™ Potassium Reagent were applied to the column. The colored trinitroanilino cryptahemispherand [2.2] and the surfactants were adsorbed on the top of the column. The nonadsorbed triethanolamine buffer, also containing 3% of 2-(2-ethoxyethoxy)-ethanol (EEE) and stabilizers, was collected and saved for later use. The trinitroanilino cryptahemispherand [2.2] and the surfactants were eluted from the column with a mixture of previously degassed isopropanol (98%) and EEE (2%). The isopropanol was removed from the eluate using an evacuated rotary evaporator at room temperature to yield an oily, dark brown concentrate.

The previously collected buffer fraction was concentrated twofold using an evacuated rotary evaporator at 35°–40° C. The concentrated trinitroanilino cryptahemispherand [2.2], the surfactants and the remaining EEE were dissolved in 400 ml of the twofold concentrated buffer solution.

The following materials were measured, added and dissolved in the above solution:

polyethylene glycol (FW 3400) 40 g
isopropanol 5.0 ml
polyvinylpyrrolidone K-29-32 0.50 g The pH of the solution was measured using an electrode pair with a calomel reference electrode to verify that the pH was less than 0.05 pH unit different from the pH of the starting ChromoLyte TM Potassium Reagent. If necessary, pH adjustment was made with a 20% triethanolamine solution or with a 20% triethanolamine HCl solution. Finally, the volume was adjusted to 500 ml with the twofold concentrated buffer solution. The reagent was filtered through a stock of media that terminated in 0.2 micron porosity. The preferred concentration of 2-(2-ethoxyethoxy)-ethanol is between about 3% and about 4.8%, and that of the polyethoxylauryl ether is between about 0.5 and about 1.0%.

The above solution when diluted 50 ml plus 50 ml with water or diluent is used to assay potassium in various clinical samples such as serum or plasma. The level of 2-(2-ethoxyethoxy)-ethanol is necessary to insure uniform freezing of the reagent and to aid in rapid resolubilization after freeze-drying. The isopropanol aids in creating the correct crystal structure during the freezing process so that the rehydration is facilitated. The BRIJ ® surfactant (e.g., BRIJ ®-35 or -58) aids in rehydration and in bubble inhibition. The polyethylene glycol is added to facilitate formation of a chemical lattice during subsequent freeze drying.

The solution was dispensed by an IVEK model AAA pump in discrete 4.0 microliter drops at a rate of 1 to 2 drops-per-second. The discrete amounts of fluid drop through air, form spheres were dried in a Virtis freezer dryer (model no. 12 EL console) until their residual moistures were less than 6% of the total remaining mass. A freeze dried reagent sphere prepared according to the above method can be reconstituted with 8 microliters of a mixture of water or diluent (14 parts) and human serum (1 part). The resulting change in absorbance at 500 nm minus the absorbance of a reagent sphere reconstituted with 8 microliters of water or diluent and minus the absorbance of the human serum sample diluted in the same ratio with water plus BRIJ ® surfactant is proportional to the amount of potassium in the sample.

The imprecision (coefficient of variation) among the 1.97 millimeter diameter spheres is:

dispensed frozen spheres 1.5% at 2.6 mg
freeze dried spheres 1.6% at 0.5 mg

Each reagent sphere dissolves in 8 microliters of water or diluent within 5 seconds. The above examples illustrate preparation of particular reagent spheres within the scope of the present invention. The examples have been provided for the purposes of clarity and understanding the invention. It will be apparent, however, that certain changes and modifications may be practiced within the scope of the appended claims.

What is claimed is:

1. A method for forming a plurality of uniform, precisely measured reagent spheres, the method consisting essentially of the steps of:

forming a homogeneous solution of a reagent;

precisely measuring uniform drops of the solution;

dispensing the uniform, precisely measured drops into an unagitated cryogenic liquid, whereby the drops are frozen;

collecting the frozen drops from the cryogenic liquid; and lyophilizing the frozen drops, thereby forming a plurality of reagent spheres having a coefficient of weight variation less than about 3% and which completely dissolve in an aqueous solution in less than about 10 seconds.

2. A method of claim 1, wherein the reagent spheres have a mean diameter between about 1.5 mm and 2.3 mm.

3. A method of claim 1, wherein the reagent spheres have a coefficient of weight variation less than about 2.5%.

4. A method of claim 1, wherein the uniform, precisely measured drops have a volume between about 2.0 $\mu l$ and about 6.5 $\mu l$.

5. A method of claim 1 wherein the homogeneous solution is degassed before dispensing uniform, precisely measured drops.

6. A method of claim 1 wherein the cryogenic liquid is liquid nitrogen.

* * * * *